US00PP25588P2

(12) United States Plant Patent
Jacobs

(10) Patent No.: US PP25,588 P2
(45) Date of Patent: May 26, 2015

(54) ***ALSTROEMERIA* PLANT NAMED 'ZAPRICLAIR'**

(50) Latin Name: *Alstroemeria hybrida*
Varietal Denomination: Zapriclair

(71) Applicant: Henricus Cornelius Maria Jacobs, Bleiswijk (NL)

(72) Inventor: Henricus Cornelius Maria Jacobs, Bleiswijk (NL)

(73) Assignee: Van Zanten Plants B.V., Rijsenhout (NL)

( * ) Notice: Subject to any disclaimer, the term of this patent is extended or adjusted under 35 U.S.C. 154(b) by 99 days.

(21) Appl. No.: 13/987,346

(22) Filed: Jul. 15, 2013

(51) Int. Cl.
*A01H 5/00* (2006.01)

(52) U.S. Cl.
USPC ..... Plt./309

(58) Field of Classification Search
USPC ..... Plt./309
See application file for complete search history.

*Primary Examiner* — Kent L Bell
(74) *Attorney, Agent, or Firm* — C. A. Whealy

(57) ABSTRACT

A new and distinct cultivar of *Alstroemeria* plant named 'Zapriclair', characterized by its compact, upright, somewhat outwardly spreading and uniformly mounded plant habit; vigorous growth habit; numerous white-colored flowers; and excellent container and garden performance.

2 Drawing Sheets

Botanical designation: *Alstroemeria hybrida.*
Cultivar denomination: 'ZAPRICLAIR'.

BACKGROUND OF THE INVENTION

The present invention relates to a new and distinct cultivar of *Alstroemeria* plant, botanically known as *Alstroemeria hybrida*, commercially used as a potted and garden-type *Alstroemeria* plant and hereinafter referred to by the name 'Zapriclair'.

The new *Alstroemeria* plant is a product of a planned breeding program conducted by the Inventor in Rijsenhout, The Netherlands. The objective of the breeding program is to create new potted *Alstroemeria* plants with uniform plant habit, freely flowering habit, attractive leaf and flower coloration and good garden performance.

The new *Alstroemeria* plant originated from a cross-pollination made by the Inventor in Rijsenhout, The Netherlands in June, 2008, of a proprietary *Alstroemeria hybrida* selection identified as code number 5874-1, not patented, as the female, or seed, parent with a proprietary *Alstroemeria hybrida* selection identified as code number 871069-2, not patented, as the male, or pollen, parent. The new *Alstroemeria* plant was discovered and selected by the Inventor as a single flowering plant from within the progeny of the stated cross-pollination in a controlled greenhouse environment in Rijsenhout, The Netherlands in August, 2009.

Asexual reproduction of the new *Alstroemeria* plant by rhizome divisions in a controlled greenhouse environment in Rijsenhout, The Netherlands since September, 2009 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Zapriclair'. These characteristics in combination distinguish 'Zapriclair' as a new and distinct potted *Alstroemeria* plant:

1. Compact, upright, somewhat outwardly spreading and uniformly mounded plant habit.
2. Vigorous growth habit.
3. Numerous white-colored flowers.
4. Excellent container and garden performance.

Plants of the new *Alstroemeria* differ primarily from plants of the female parent selection in flower color as plants of the female parent selection have stripes on the perianth segments.

Plants of the new *Alstroemeria* differ primarily from plants of the male parent selection in plant habit as plants of the new *Alstroemeria* are more compact than plants of the male parent selection. In addition, plants of the new *Alstroemeria* and the male parent selection differ in flower color as plants of the male parent selection have yellow-colored flowers.

Plants of the new *Alstroemeria* can be compared to plants of *Alstroemeria hybrida* 'Staprilene', disclosed in U.S. Plant Pat. No. 11,683. In side-by-side comparisons conducted in Rijsenhout, The Netherlands, plants of the new *Alstroemeria* differed primarily from plants of 'Staprilene' in the following characteristics:

1. Plants of the new *Alstroemeria* were larger than plants of 'Staprilene'.
2. Plants of the new *Alstroemeria* flowered earlier than plants of 'Staprilene'.
3. Plants of the new *Alstroemeria* had larger flowers than plants of 'Staprilene'.
4. Plants of the new *Alstroemeria* and 'Staprilene' differed slightly in flower color.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet comprises a side perspective view of a typical flowering plant of 'Zapriclair' grown in a container.

The photograph on the second sheet is a close-up view of a typical flowering plant of 'Zapriclair'.

DETAILED BOTANICAL DESCRIPTION

The aforementioned photographs and following observations and measurements describe plants of the new *Alstroemeria* grown during the late winter and spring in 14-cm containers in a glass-covered greenhouse in Rijsenhout, The Netherlands. During the production of the plants, day temperatures ranged from 15° C. to 25° C., night temperatures ranged from 10° C. to 15° C. and light levels averaged 5,000 lux. Plants were three months old when the photographs and the description were taken. In the following description, color references are made to The Royal Horticultural Society Colour Chart, 2007 Edition, except where general terms of ordinary dictionary significance are used.

Botanical classification: *Alstroemeria hybrida* 'Zapriclair'.

Parentage:

- *Female, or seed, parent*.—Proprietary *Alstroemeria hybrida* selection identified as code number 5874-1, not patented.
- *Male or pollen parent*.—Proprietary *Alstroemeria hybrida* selection identified as code number 871069-2, not patented.

Propagation:

- *Type*.—In vitro rhizogenesis.
- *Time to produce a rooted young plant, summer*.—About 40 days.
- *Time to produce a rooted young plant, winter*.—About 60 days.
- *Root description*.—Fibrous, fleshy, thick; close to 155D in color.
- *Rooting habit*.—Freely branching; medium density.
- *Rhizomes*.—Shape: Elongate; rounded. Length: About 10 cm to 30 cm. Diameter: About 3 mm to 10 mm. Texture: Smooth. Color: Close to 155D.

Overall plant description:

- *Plant and growth habit*.—Compact, upright, somewhat outwardly spreading and uniformly mounding plant habit; freely branching habit, dense and bushy appearance; vigorous growth habit.
- *Plant height*.—About 28 cm to 30 cm.
- *Plant diameter (spread)*.—About 40 cm to 45 cm.

Lateral branch description:

- *Aspect*.—Mostly upright.
- *Length*.—About 20 cm to 22 cm.
- *Diameter*.—About 3 mm.
- *Internode length*.—About 1.5 cm to 2.5 cm.
- *Strength*.—Strong.
- *Texture*.—Smooth, glabrous.
- *Color*.—Close to 138C.

Leaf description:

- *Appearance*.—Simple, asymmetrical; sessile.
- *Length*.—About 7 cm to 9 cm.
- *Width*.—About 2.5 cm to 3.5 cm.
- *Shape*.—Lanceolate.
- *Apex*.—Acute.
- *Base*.—Cuneate.
- *Margin*.—Entire.
- *Texture, upper and lower surfaces*.—Smooth, glabrous.
- *Venation pattern*.—Parallel.
- *Color*.—Developing and fully expanded leaves, upper surface: Close to 138A; venation, close to 141D. Developing and fully expanded leaves, lower surface: Close to N138C; venation, close to 137D.

Flower description:

- *Flower type and habit*.—Single cup-shaped flowers arranged in compound umbels; flowers face mostly outwardly; perianth segments separate; freely flowering habit with five to seven flowers per inflorescence.
- *Natural flowering season*.—Flowering continuous during the spring in The Netherlands; early flowering habit, plants begin flowering about 70 to 80 days after planting.
- *Fragrance*.—None detected.
- *Flower longevity on the plant*.—About four weeks; flowers not persistent.
- *Flower buds*.—Length: About 4.3 cm to 4.5 cm. Diameter: About 2 cm to 2.5 cm. Shape: Roughly ovoid. Color: Close to 143D.
- *Umbel height*.—About 8 cm to 9 cm.
- *Umbel diameter*.—About 14 cm to 15 cm.
- *Flower diameter*.—About 8 cm.
- *Flower depth*.—About 6 cm to 6.5 cm.
- *Perianth*.—Arrangement: Six arranged in two whorls, each whorl with two lateral and one median segments. Inner perianth, lateral segments: Length: About 5.5 cm. Width: About 2.5 cm. Shape: Oblanceolate. Apex: Wishbone-shaped. Base: Attenuate. Margin: Shallowly serrated; weakly undulate. Texture, upper and lower surfaces: Smooth, glabrous. Color, when opening, upper and lower surfaces: Close to 155C. Color, fully opened, upper surface: Close to NN155C; towards the base, close to 8D; at the base, close to NN155D; stripes, close to 185B; venation, close to 148D; apical point, close to 146C. Color, fully opened, lower surface: Close to NN155C; towards the base, close to 11D; at the base, close to NN155D. Inner perianth, median segment: Length: About 5 cm. Width: About 2.5 cm. Shape: Oblanceolate. Apex: Wishbone-shaped. Base: Attenuate. Margin: Shallowly serrated; weakly undulate. Texture, upper and lower surfaces: Smooth, glabrous. Color, when opening, upper and lower surfaces: Close to 155A. Color, fully opened, upper surface: Close to 155A; venation, close to 148D; apical point, close to 146C. Color, fully opened, lower surface: Close to 155A. Outer perianth, lateral segments: Length: About 5.8 cm to 6 cm. Width: About 4.3 cm to 4.6 cm. Shape: Obovate. Apex: Emarginate with an embedded point. Base: Attenuate. Margin: Shallowly serrate; weakly undulate. Texture, upper and lower surfaces: Smooth, glabrous. Color, when opening, upper and lower surfaces: Close to 155A. Color, fully opened, upper surface: Close to 155C; venation, close to 189B; apical point, close to 137B. Color, fully opened, lower surface: Close to 155C. Outer perianth, median segment: Length: About 5.5 cm to 5.8 cm. Width: About 4.3 cm to 4.5 cm. Shape: Obovate. Apex: Emarginate with an embedded point. Base: Attenuate. Margin: Shallowly serrate; weakly undulate. Texture, upper and lower surfaces: Smooth, glabrous. Color, when opening, upper and lower surfaces: Close to 155A. Color, fully opened, upper surface: Close to 155C; venation, close to 189B; apical point, close to 137B. Color, fully opened, lower surface: Close to 155C.

*Pedicels*.—Length: About 5 mm to 10 mm. Diameter: About 1.5 mm to 2 mm. Strength: Strong. Angle: About 30° from vertical. Texture: Smooth, glabrous. Color: Close to 147C.

*Reproductive organs*.—Stamens: Quantity per flower: Typically six. Anther shape: Elliptic. Anther length: About 2 mm. Anther color: Close to 160C. Pollen amount: Scarce. Pollen color: Close to 13A. Pistils: Quantity per flower: One. Style length: About 4.3 cm to 4.5 cm. Style color: Close to 69A. Stigma shape: Three-parted. Stigma color: Close to 69D. Ovary color: Close to 145A.

*Fruits and seeds*.—Fruit and seed development have not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have excellent garden performance and to tolerate wind, rain and temperatures from about −5° C. to about 40° C.

It is claimed:

1. A new and distinct *Alstroemeria* plant named 'Zapriclair' as illustrated and described.

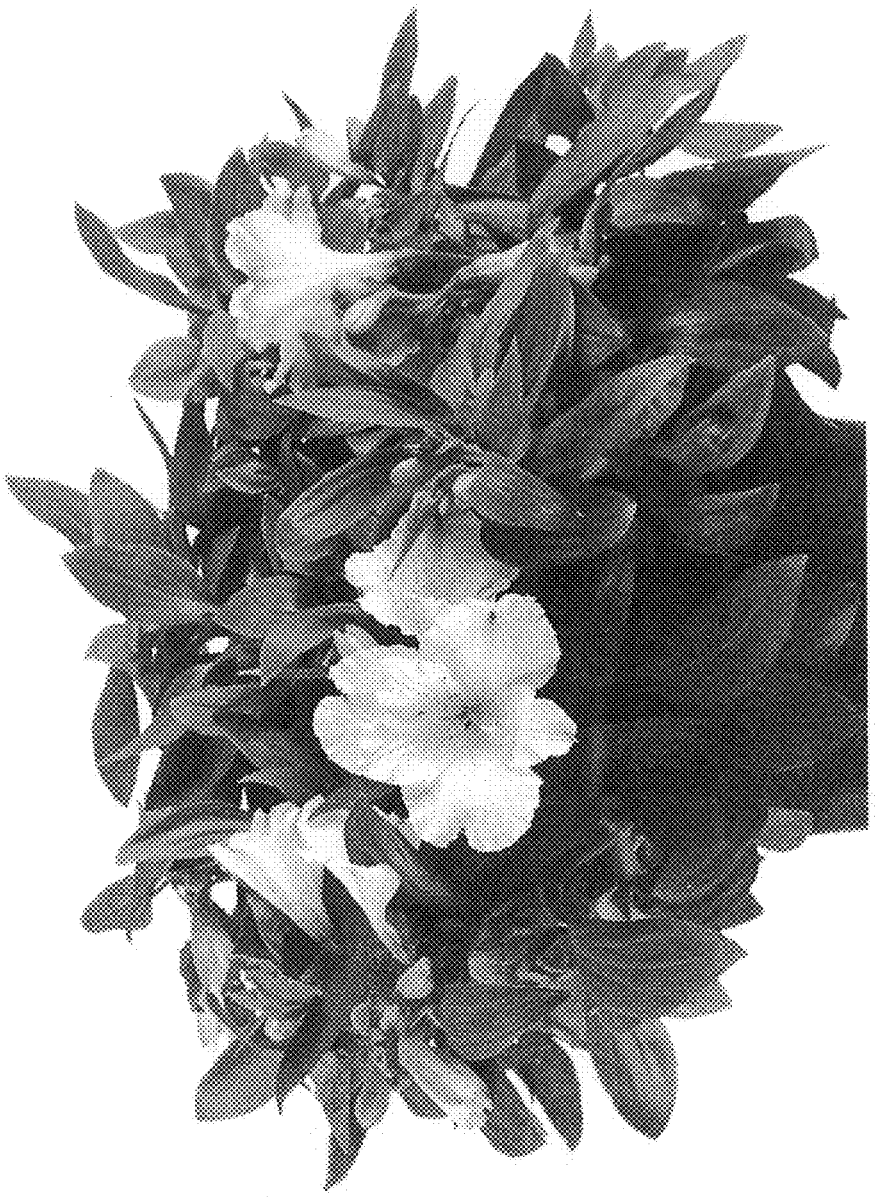

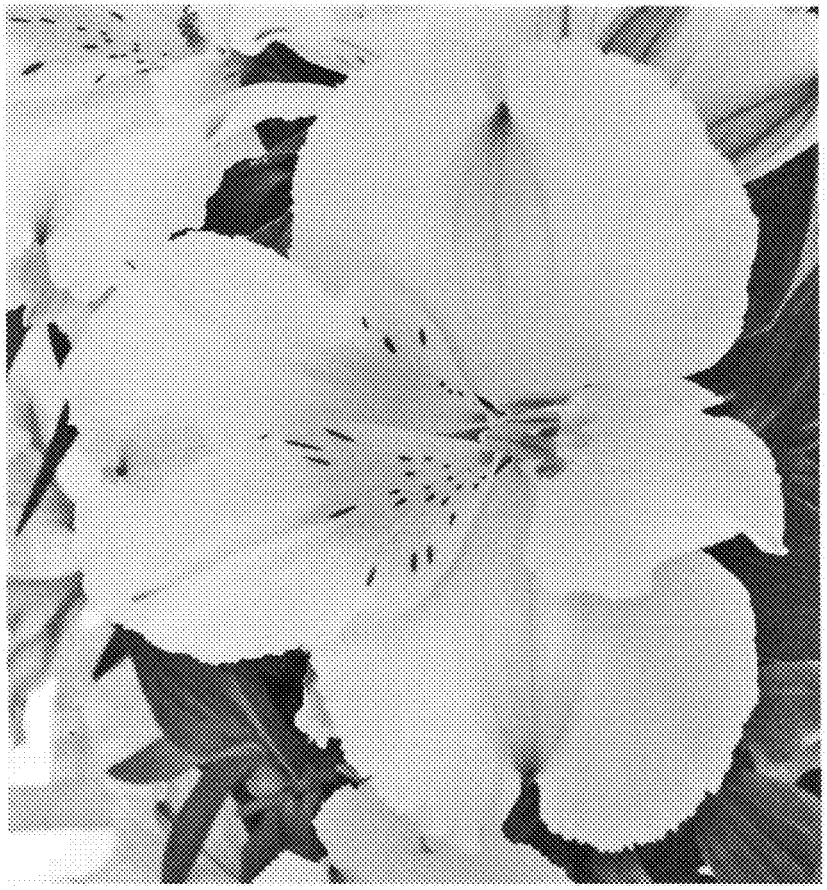

* * * * *